US008620993B2

(12) United States Patent
Kim et al.

(10) Patent No.: US 8,620,993 B2
(45) Date of Patent: Dec. 31, 2013

(54) ACTIVITY MONITORING SYSTEM AND METHOD FOR TRANSMITTING INFORMATION FOR ACTIVITY MONITORING

(75) Inventors: Min Ho Kim, Daejeon (KR); Jae Won Jang, Daejeon (KR); Ho Youl Jung, Daejeon (KR); Sa Kwang Song, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 1171 days.

(21) Appl. No.: 12/505,566

(22) Filed: Jul. 20, 2009

(65) Prior Publication Data

US 2010/0161706 A1 Jun. 24, 2010

(30) Foreign Application Priority Data

Dec. 23, 2008 (KR) ........................ 10-2008-0132569

(51) Int. Cl.
*G06F 15/16* (2006.01)
(52) U.S. Cl.
USPC .......................................... 709/202; 709/248
(58) Field of Classification Search
USPC .......................................................... 709/202
See application file for complete search history.

(56) References Cited

U.S. PATENT DOCUMENTS

| 7,366,645 | B2 | 4/2008 | Ben-Arie | |
|---|---|---|---|---|
| 7,421,369 | B2 | 9/2008 | Clarkson | |
| 2001/0048368 | A1* | 12/2001 | Lehrman et al. | 340/669 |
| 2003/0208335 | A1 | 11/2003 | Unuma et al. | |
| 2005/0171410 | A1* | 8/2005 | Hjelt et al. | 600/300 |
| 2005/0245793 | A1* | 11/2005 | Hilton et al. | 600/300 |
| 2006/0284979 | A1 | 12/2006 | Clarkson | |
| 2007/0173705 | A1* | 7/2007 | Teller et al. | 600/300 |
| 2007/0208530 | A1 | 9/2007 | Vock et al. | |
| 2008/0133277 | A1 | 6/2008 | Jang et al. | |

(Continued)

FOREIGN PATENT DOCUMENTS

| JP | 10-113343 A | 5/1998 |
|---|---|---|
| JP | 2003-061935 A | 3/2003 |

(Continued)

OTHER PUBLICATIONS

Jaewon Jang, et al; "An Effective Method for Component Activity Classification Supporting Location Awareness and User Identification" Engineering in Medicine and Biology Society, 2008. EMBC 2008, pp. 5258-5261.

*Primary Examiner* — Lynn Feild
*Assistant Examiner* — Lin Liu
(74) *Attorney, Agent, or Firm* — Ladas & Parry LLP (57) ABSTRACT

An activity monitoring system and method are disclosed to reduce the size of an activity sensor device to reduce its power consumption and smoothly transmit activity and occupancy information from the activity sensor device and an occupancy sensor device to an activity monitoring server to monitor an individual's activity and occupancy information. The activity monitoring system includes: an activity sensor device configured to detect a physical activity of a user, classify the detected physical activity, and transmit activity classification information as a result along with user identification information; one or more occupancy sensor devices configured to receive the activity classification information and the individual's identification information from the activity sensor device, and transmit the received information along with occupancy information; and an activity monitoring server configured to manage the activity classification information, the occupancy information, and the individual's identification information received from the occupancy sensor devices.

21 Claims, 4 Drawing Sheets

(56) References Cited

U.S. PATENT DOCUMENTS

| | | |
|---|---|---|
| 2008/0155077 A1 | 6/2008 | James |
| 2008/0176655 A1 | 7/2008 | James et al. |
| 2008/0182724 A1 | 7/2008 | Guthrie |
| 2008/0197881 A1 | 8/2008 | Bertin |
| 2008/0255626 A1* | 10/2008 | Fricke et al. ............ 607/11 |
| 2009/0131761 A1* | 5/2009 | Moroney III et al. ...... 600/301 |
| 2010/0160744 A1 | 6/2010 | Ha et al. |

FOREIGN PATENT DOCUMENTS

| | | |
|---|---|---|
| JP | 2003-317174 A | 11/2003 |
| KR | 1020030043178 A | 6/2003 |
| KR | 1020030070495 A | 8/2003 |
| KR | 10-0525623 B1 | 10/2005 |
| KR | 1020060099580 A | 9/2006 |
| KR | 1020070036836 A | 4/2007 |
| KR | 1020070091969 A | 9/2007 |
| KR | 10-0776798 B1 | 11/2007 |
| KR | 10-0795110 B1 | 1/2008 |
| KR | 1020080009167 A | 1/2008 |
| KR | 10-0813166 B1 | 3/2008 |
| KR | 1020080050993 A | 6/2008 |
| KR | 1020080051013 A | 6/2008 |
| KR | 1020080084127 A | 9/2008 |
| KR | 1020080106830 A | 12/2008 |

* cited by examiner

ACTIVITY MONITORING SYSTEM AND METHOD FOR TRANSMITTING INFORMATION FOR ACTIVITY MONITORING

CROSS-REFERENCE TO RELATED APPLICATIONS

This application claims the priority of Korean Patent Application No. 2008-0132569 filed on Dec. 23, 2008, in the Korean Intellectual Property Office, the disclosure of which is incorporated herein by reference.

BACKGROUND OF THE INVENTION

1. Field of the Invention

The present invention relates to an activity monitoring system and method for transmitting information for activity monitoring, and more particularly, to an activity monitoring system capable of reducing the power consumption of an activity sensor device by reducing the size of the activity sensor device and smoothly transmitting activity and occupancy information from the activity sensor device and an occupancy sensor device to an activity monitoring server to monitor a user's activity and occupancy information, and a method for transmitting information for activity monitoring.

2. Description of the Related Art

As modern society is increasingly faced with the reality of a rapidly increasing aging population, the importance of monitoring the health of senior citizens to ensure their security at home is paramount.

However, most health monitoring is largely focused on the measurement of the bio-signals of human bodies (i.e., individuals), rather than monitoring the activities of individuals. Even if user's activities are monitored, the monitoring is limited to very simple activities such as falls.

Activity monitoring refers to monitoring all of an individual's concrete physical activities (e.g., sitting, standing, lying, walking, running, etc.). If the individual's concrete activity information is combined with information concerning the individual's occupancy of furniture such as a couch or a bed or the user's location information, more useful information can be obtained to be used for multiple health monitoring services.

The information obtained from activity monitoring may be used for analyzing an individual's activity patterns, and through the analysis, the information can be used to help correct any undesirable activity to help maintain the individual's health. Thus, research on activity monitoring is actively ongoing.

The related art for activity monitoring includes a US Laid Open Publication No. 2006/0284979 A1 (Entitled Activity recognition apparatus, method and program). This art was devised to recognize an activity of a sensor wearer by using a linear motion sensor and a rotational motion sensor. However, this related art provides classification of the sensor wearer's activities such as walking, running, lying, and the like, but fails to provide furniture usage information or location detection function.

In addition, a technique that recognizes various daily activities upon detecting the use of a basic activity sensor by an individual has been presented. However, this technique merely uses occupancy information concerning individual's occupancy of furniture or the like, without combining this with an individual's activity information, so it lacks the ability to monitor the individual's physical activities.

Further, a technique that wirelessly monitors various bio-signals to detect a fall or an individual's location has been developed, but it has a problem in that the monitoring activity is limited to a fall. In addition, with this technique, the detected location is somewhat inaccurate, allowing only a rough estimation of the individual's location, and the accuracy of detecting the location is degraded due to the presence of obstacles.

SUMMARY OF THE INVENTION

An aspect of the present invention provides an activity monitoring system capable of accurately analyzing an individual's activity and recognizing an accurate location of the user by using an activity sensor worn by the user and an occupancy sensor attached to fixed objects or items such as furniture, and a method for transmitting information for activity monitoring.

Another aspect of the present invention provides an activity monitoring system capable of reducing power consumption by shortening a transmission range of an activity sensor worn by a user and recognizing an accurate location based on the short transmission range.

According to an aspect of the present invention, there is provided an activity monitoring system including: an activity sensor device configured to detect an individual's physical activity, classify the detected physical activity, and transmit activity classification information as a result, along with user identification information; one or more occupancy sensor devices configured to receive the activity classification information and the user identification information from the activity sensor device, and transmit the received information along with occupancy information; and an activity monitoring server configured to manage the activity classification information, the occupancy information, and the user identification information received from the occupancy sensor devices.

According to another aspect of the present invention, there is provided a method for transmitting information for activity monitoring by an occupancy sensor device in an activity monitoring system including an activity sensor device worn by a user, one or more occupancy sensor devices, and an activity monitoring server, the method including: receiving activity classification information and user identification information obtained by detecting a physical activity of a user from a connection-established activity sensor device by using a first propagation; and transmitting the activity classification information and the user identification information along with occupancy information to the activity monitoring server by using a second propagation.

According to another aspect of the present invention, there is provided a method for transmitting information for activity monitoring by an activity sensor device in an activity monitoring system including the activity sensor device worn by a user, one or more occupancy sensor devices, and an activity monitoring server, the method including: detecting an activity of a user and classifying the detected signal; generating activity classification information by using the classified signal; establishing a connection to the one or more occupancy sensor devices; and transmitting the generated activity classification information and the user identification information to the connection-established occupancy sensor devices by using a first propagation with a short transmission range, so that the activity classification information and the user identification information can be transmitted along with occupancy information to the activity monitoring server.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will now be described in detail with reference to the accompanying drawings. The invention may however be embodied in many different forms and should not be construed as limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

Figure 1:
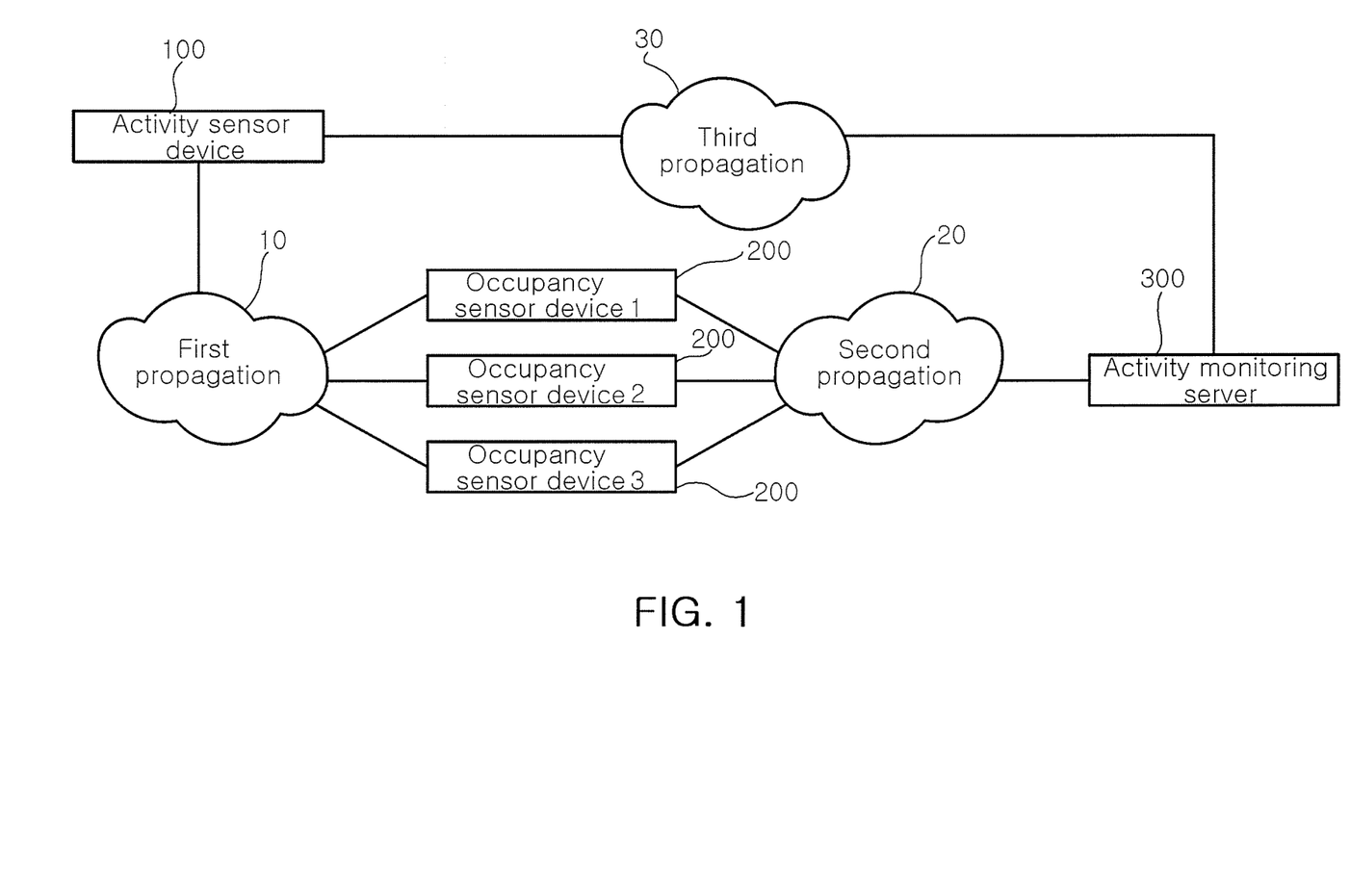
FIG. 1 is a schematic block diagram illustrating the configuration of an activity monitoring system according to an exemplary embodiment of the present invention.

FIG. 1 is a schematic block diagram illustrating the configuration of an activity monitoring system according to an exemplary embodiment of the present invention.

As illustrated, the activity monitoring system includes an activity sensor device 100, one or more occupancy sensor devices 200 installed at particular positions such as furniture or the like, and an activity monitoring server 300 for receiving information transferred from the activity sensor device 100 and the occupancy sensor devices 200 and performing activity monitoring.

The activity sensor device 100 detects an individual's activity and classifies the detected activity. For example, the activity sensor device 100 detects and classifies activities such as sitting, standing, lying, walking, running, falling, etc. The individual's activity information, detected by the activity sensor device 100, is called activity classification information. The activity sensor device 100 may include diverse sensors that can detect and classify human body activities, such as an acceleration sensor, a geomagnetic sensor (i.e., magnetometer sensor), or a combination thereof.

When the activity sensor device 100 detects the activity of the user, it transfers the activity classification information, namely, the result, to the occupancy sensor devices 200. In addition, the activity sensor device 100 also transfers user identification information identifying the user along with the activity classification information to the occupancy sensor devices 200.

In this case, in order for the activity sensor device 100 to transfer the activity classification information and the user identification information to the occupancy sensor devices 200, a connection must be established between the activity sensor device 100 and the one or more occupancy sensor devices 200.

The activity sensor device 100 uses propagation (i.e., radiowaves) with a (relatively) short transmission range in comparison to that of the occupancy sensor devices 200. Hereinbelow, the propagation used by the activity sensor device 100 to transfer information to the occupancy sensor devices 200 will be referred to as a first propagation 10.

The first propagation 10 used by the activity sensor device 100 may have a transmission range of, for example, 0.5 m to 1 m. Thus, in order for the activity sensor device 100 to establish a connection with at least one occupancy sensor device 200, the occupancy sensor device 200 must be within the transmission range of the activity sensor device 100. Thus, when the one or more occupancy sensor devices 200 and the activity sensor device 100 are within the transmission range of the first propagation 10, the occupancy sensor devices 200 detect a signal from the activity sensor device 100 and a connection is established therebetween.

In this case, if no connection is established between the activity sensor device 100 and the one or more occupancy sensor devices 200, the activity sensor device 100 stores the activity classification information, the detected user's activity, in its internal database (not shown), and then, when a connection is established, the activity sensor device 100 transfers the stored activity classification information to the connected occupancy sensor devices 200. And the activity sensor device 100 also deletes the stored information from the database (not shown).

Unless the activity sensor device 100 is connected to the one or more occupancy sensor devices 200, the activity sensor device 100 transmits the detected activity classification information and the individual's identification information directly to the activity monitoring server 300 by using a third propagation 30.

Here, the third propagation 30 has a broader transmission range than that of the first propagation 10. Thus, the activity sensor device 100 can transfer information to the activity monitoring server 300 regardless of its location.

Thereafter, when a connection is established between the activity sensor device 100 and the one or more occupancy sensor devices 200, the activity sensor device 100 stops transmission of information via the third propagation 30 and transmits the activity classification information and the user identification information to the connection-established occupancy sensor devices 200 by using the first propagation 10.

The occupancy sensor devices 200 are installed at furniture such as a couch or a bed or at any particular locations desired to be checked for an individual's occupation, so in the event of the individual's occupation (i.e., when certain furniture is being used by the individual), a corresponding occupancy sensor device 200 detects a corresponding state.

In addition, the occupancy sensor devices 200 receive the activity classification information and the individual's identification information from the connection-established activity sensor device 100 and transmit them along with the detected occupancy information to the activity monitoring server 300 via a second propagation 20. Here, the second propagation 20 has a (relatively) broad transmission range. Accordingly, when an individual's occupation is detected, when the activity classification information and the user identification information are received from the activity sensor device 100, or on a periodical basis, the occupancy sensor devices 200 may transmit information by using the second propagation 20.

Referring to how the occupancy sensor devices 200 detect an individual's occupation, the occupancy sensor devices 200 may detect an individual's occupation via a sensor that can detect the individual's occupation by itself, such as a pressure sensor or the like. In addition, when a signal is received from the activity sensor device 100 via the first propagation with a narrow transmission range, the occupancy sensor devices 200 may detect (recognize) an individual's occupation.

Thus, the occupancy sensor devices 200 may transmit occupancy information to the activity monitoring server 300 when an individual's occupation is detected, or periodically. Of course, in the presence of the connection-established activity sensor device 100, the occupancy sensor devices 200 may transmit the activity classification information and the individual's identification information, which are transferred from the activity sensor device, 100, along with the occupancy information to the activity monitoring sever 300, just as with a gateway.

Upon receiving the activity classification information, the occupancy information, or a combination thereof, the activity monitoring server 300 manages them in various manners as necessary. In addition, the activity monitoring server 300 makes them ready for being applied to a required application.

The activity monitoring system, according to an exemplary embodiment of the present invention, may perform activity tracking through the activity sensor device 100, the occupancy sensor devices 200, and the activity monitoring server 300 as follows.

First, the activity sensor device 100 classifies an individual's activities periodically. And then, when the individual approaches the occupancy sensor devices 200 in the house, a signal of the activity sensor device 100 is received by the occupancy sensor device 200 by using the first propagation 10 with a short transmission range. The occupancy sensor device 200 combines the received activity classification information and the occupation status and transmits the combined activity classification information to the activity monitoring server 300 by using the second propagation 20.

An example of the combined activity classification information is as follows. For example, in case of a couch, combined activity classification information when the individual simply comes to the vicinity of the couch would be "activity: standing/location: couch". Combined activity classification information when the individual actually sits on the couch would be "activity: sitting on couch/location: couch". In this case, when the activity and a change in the occupation state of the couch are consistent within a certain range, it is determined as "sitting on couch".

Besides the combined activity classification information, the individual identification information of the activity sensor device 100 is also transmitted to the activity monitoring server 300.

Figure 2:
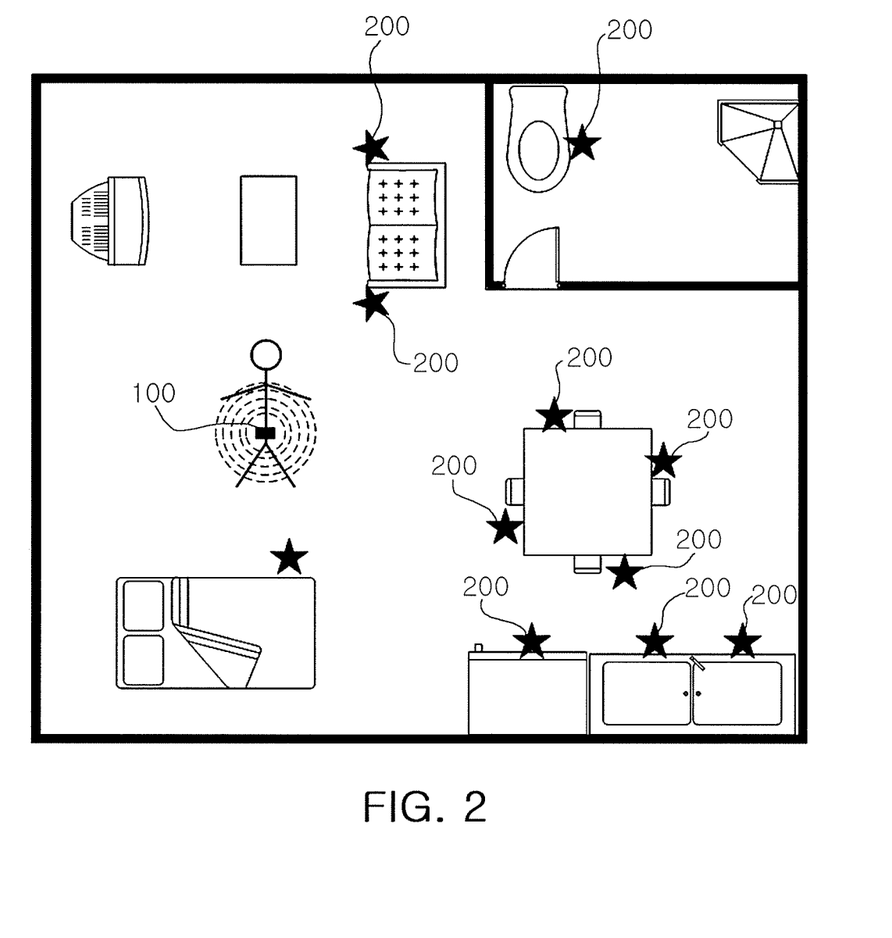
FIG. 2 illustrates a state in which an activity sensor device and occupancy sensor devices are actually installed according to an exemplary embodiment of the present invention.

FIG. 2 illustrates a state in which an activity sensor device and occupancy sensor devices are actually installed according to an exemplary embodiment of the present invention.

As illustrated, the activity sensor device 100 is attached to the individual's body, detects an individual's activity, and transmits required information by using the first propagation. In this case, the first propagation has a very narrow transmission range as shown in FIG. 2.

The occupancy sensor devices 200 may be attached to various locations such as a couch, a bed, a table, chairs, a refrigerator, a sink, a bathroom fixture, and the like, as illustrated. Accordingly, the occupancy sensor devices 200 receive a signal transferred from the activity sensor device 100 via the first propagation according to the movement of the user.

Figure 3:
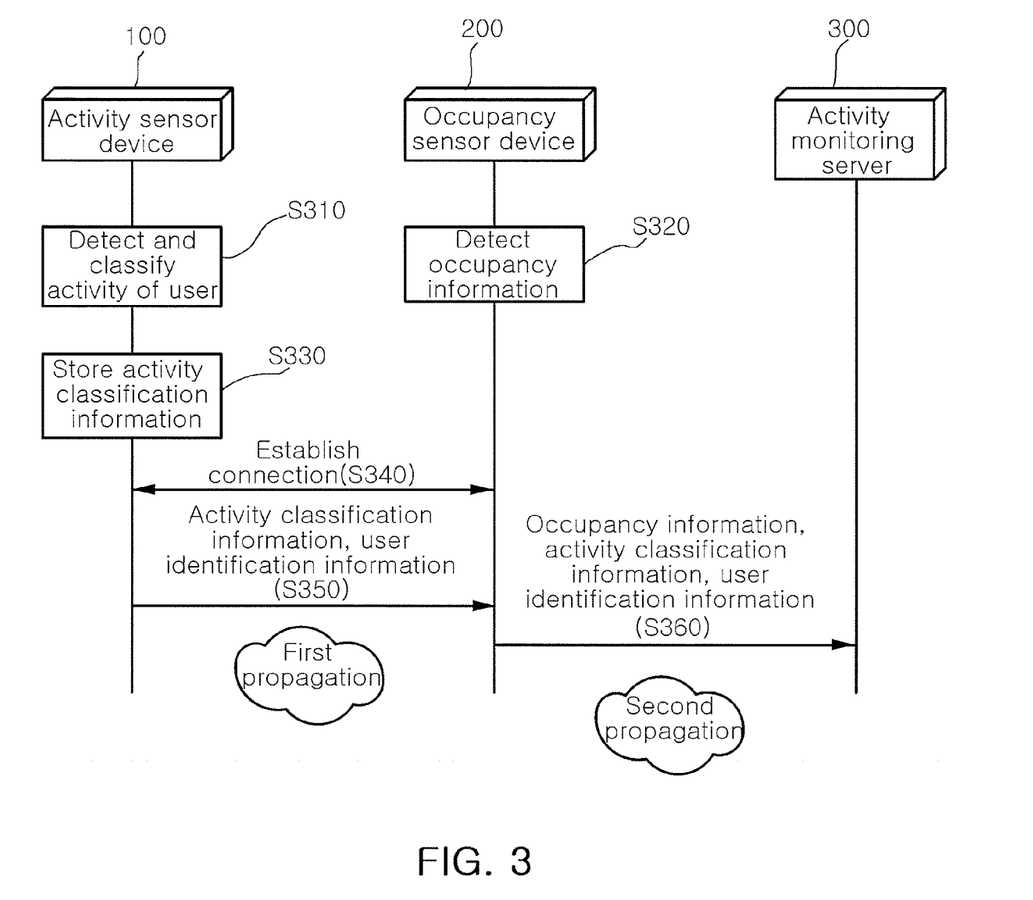
FIG. 3 is a flow chart illustrating the process of an activity monitoring method according to a first exemplary embodiment of the present invention.

FIG. 3 is a flow chart illustrating the process of an activity monitoring method according to a first exemplary embodiment of the present invention.

Specifically, FIG. 3 shows the process of storing activity classification information detected by the activity sensor device 100 unless a connection is established between the activity sensor device 100 and the one or more occupancy sensor devices 200.

First, the activity sensor device 100 continuously detects an individual's activity and generates activity classification information (S310). The activity classification information generated thusly is stored in the internal database of the activity sensor device 100 (S330).

Meanwhile, the occupancy sensor devices 200 continuously detect whether or not the locations where they are installed are occupied by the individual, regardless of whether or not a signal is received from the activity sensor device 100 (S320). The occupancy sensor devices 200 periodically transmit corresponding information to the activity monitoring server 300.

In addition, the activity sensor device 100 periodically transmits an occupancy sensor search signal using the first propagation. Thus, when a search signal of the activity sensor device 100 is detected as the user is within the range of a specific occupancy sensor device in the house, a connection is established between the activity sensor device 100 and the corresponding occupancy sensor device 200 (S340)

With the connection established therebetween, the activity classification information stored in the activity sensor device 100 is transmitted to the corresponding occupancy sensor device 200 by using the first propagation (S350). The activity sensor device 100 deletes the stored activity classification information.

The occupancy sensor device 200 transmits the received activity classification information to the activity monitoring server 300 (S360).

Thereafter, as for activity classification information received after the activity sensor device 100 and the occupancy sensor device 200 are connected, the activity classification information, individual's identification information, and the occupancy information are generated and then transmitted to the activity monitoring server 300 in the same manner as described above with reference to FIG. 1.

Figure 4:
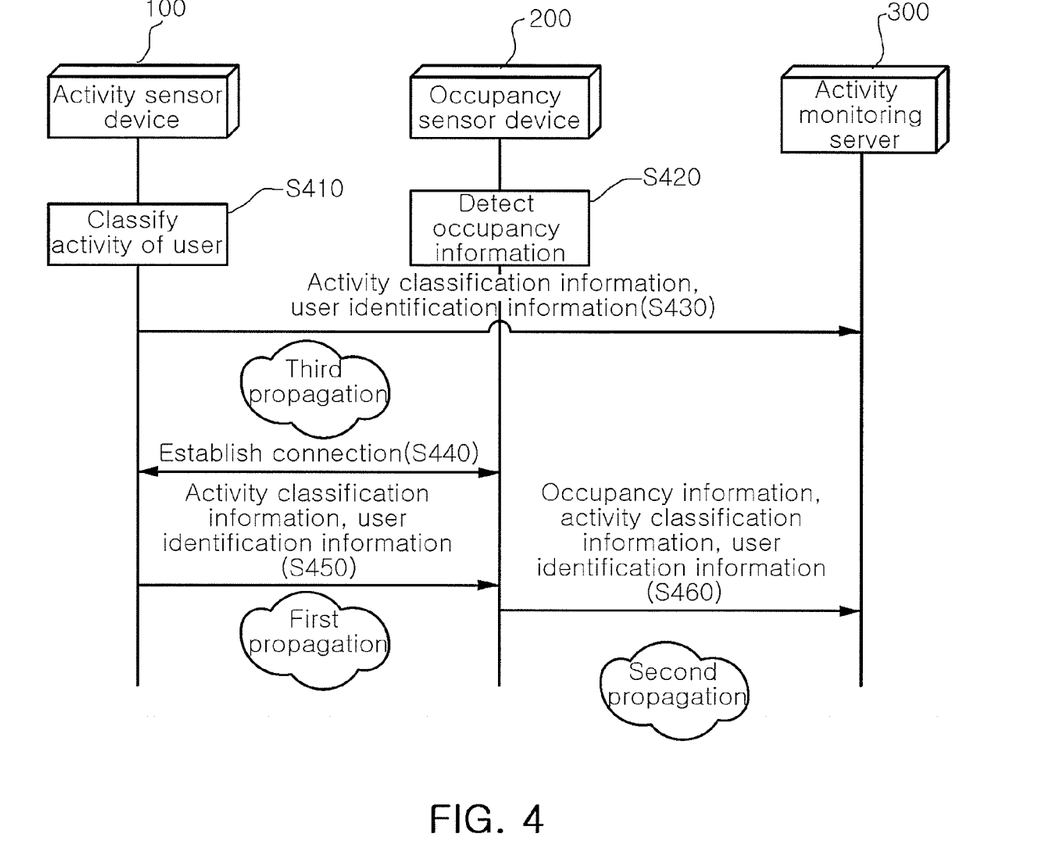
FIG. 4 is a flow chart illustrating the process of an activity monitoring method according to a second exemplary embodiment of the present invention.

FIG. 4 is a flow chart illustrating the process of an activity monitoring method according to a second exemplary embodiment of the present invention.

Specifically, FIG. 4 shows the process of transmitting activity classification information and user identification information by the activity sensor device 100 directly to the activity monitoring server 300 by using the third propagation 30 with a broad transmission range unless a connection is established between the activity sensor device 100 and the one or more occupancy sensor devices 200.

First, the activity sensor device 100 continuously detects a user's activity and generates activity classification information (S410). Meanwhile, the occupancy sensor devices 200 also periodically detect whether or not the locations where they are installed are occupied by the individual regardless of whether or not a signal is received from the activity sensor device 100 (S420). The activity sensor device 100 also periodically transmits corresponding information to the activity monitoring server 300.

If a connection has not been established between the activity sensor device 100 and the occupancy sensor devices 200, the activity sensor device 100 transmits the detected activity classification information directly to the activity monitoring server 300 by using the third propagation (strong transmission propagation) with a broad transmission range (S430).

At this time, the activity sensor device 100 periodically transmits an occupancy sensor search signal by using the first propagation 10 (a weak transmission propagation with a narrow transmission range).

When a search signal of the activity sensor device 100 is detected as the user comes near a certain occupancy sensor device 200 in the house, a connection is established between the activity sensor device 100 and the corresponding occupancy sensor device 200 (S440).

With the connection established therebetween, the activity sensor device 100 does not transmit the activity classification information to the activity monitoring server 300 by using the third propagation 30 any longer.

Instead, the activity sensor device 100 transmits the activity classification information to the occupancy sensor device 200 by using the first propagation (S450), and the occupancy sensor device 200 transmits both the received activity classification information and the reception information to the activity monitoring server 300 (S460).

Thereafter, as for activity classification information received after the activity sensor device 100 and the occupancy sensor device 200 are connected, the activity classification information, individual's identification information, and the occupancy information are generated and then transmitted to the activity monitoring server 300 in the same manner as described above with reference to FIG. 1.

As set forth above, the activity monitoring system and method according to exemplary embodiments of the invention have the advantages that because the transmission range of the activity sensor is short, the power consumption of the activity sensor device can be reduced, and as a result, the activity sensor device can be reduced in size by using a small battery. In addition, because the activity information of the activity sensor having the short transmission range is transmitted to the activity monitoring server via the occupancy sensor device, an accurate location can be recognized (detected).

While the present invention has been shown and described in connection with the exemplary embodiments, it will be apparent to those skilled in the art that modifications and variations can be made without departing from the spirit and scope of the invention as defined by the appended claims.

What is claimed is:

1. An activity monitoring system comprising:
    an activity sensor device configured to detect an individual's physical activity, classify the detected physical activity, and transmit activity classification information as a result along with the individual's identification information;
    one or more occupancy sensor devices configured to receive the activity classification information and the individual's identification information from the activity sensor device, and transmit the received information along with occupancy information; and
    an activity monitoring server configured to manage the activity classification information, the occupancy information, and the individual's identification information received from the occupancy sensor devices,
    wherein the activity sensor device is configured to transmit the activity classification information and the individual's identification information to the one or more occupancy sensor devices or the activity monitoring server, and
    wherein the activity sensor device is configured to transmit the activity classification information and the individual's identification information to the one or more occupancy sensor devices having a first power, and
    wherein the activity sensor device is configured to transmit the activity classification information and the individual's identification information to the activity monitoring server having a second power.

2. The system of claim 1, wherein when a connection is established between the activity sensor device and the one or more occupancy sensor devices, the activity sensor device transmits the activity classification information and the individual's identification information to the one or more occupancy sensor by using a first propagation with a short transmission range.

3. The system of claim 2, wherein unless the activity sensor device is connected to the one or more occupancy sensor devices, the activity sensor device transmits the activity classification information and the individual's identification information directly to the activity monitoring server by using a third propagation with a broad transmission range.

4. The system of claim 3, wherein when a connection is established between the activity sensor device and the one or more occupancy sensor devices, the activity sensor device uses only the first propagation and stops the transmission of information via the third propagation.

5. The system of claim 1, wherein unless the activity sensor device is connected to the one or more occupancy sensor devices, the activity sensor device stores the activity classification information in a database.

6. The system of claim 5, wherein when the activity sensor device is connected to the one or more occupancy sensor devices, the activity sensor device transmits the activity classification information stored in the database to the occupancy sensor devices and then deletes the activity classification information from the database.

7. The system of claim 1, wherein the activity sensor device comprises at least one of an acceleration sensor and a geomagnetic sensor.

8. The system of claim 1, wherein the one or more occupancy sensor devices transmit the activity classification information, the occupancy information, and the individual's identification information to the activity monitoring server by using a second propagation with a broader transmission range than that of the first propagation received from the activity sensor device.

9. The system of claim 1, wherein the occupancy sensor devices periodically transmit the occupancy information to the activity monitoring server.

10. The system of claim 1, wherein only when a signal is received from the activity sensor device, the occupancy sensor devices transmit the signal to the activity monitoring server.

11. The system of claim 1, wherein only when a connection between the occupancy sensor devices and the activity sensor device is established, the occupancy sensor devices transmit a signal to the activity monitoring server.

12. A method for transmitting information for activity monitoring by an occupancy sensor device in an activity monitoring system comprising an activity sensor device worn by an individual, one or more occupancy sensor devices, and an activity monitoring server, the method comprising:
    receiving from the activity sensor device activity classification information and the individual's identification information obtained by detecting a physical activity of a user from a connection-established activity sensor device by using a first propagation; and
    transmitting the activity classification information and the individual's identification information along with occupancy information to the activity monitoring server by using a second propagation,
    wherein the activity sensor device transmits the activity classification information and the individual's identification information having a first power or a second power, wherein the first power is less than the second power, and
when the activity sensor device transmits the activity classification information and the individual's identification information to the one or more occupancy sensor devices then the activity sensor device only transmits the activity classification information and the individual's identification information to the one or more occupancy sensor devices having the first power.

13. The method of claim 12, wherein the occupancy information is periodically transmitted by the occupancy sensor device to the activity monitoring server.

14. The method of claim 12, wherein the occupancy information is transmitted by the occupancy sensor device to the activity monitoring server, only when a signal is received from the activity sensor device.

15. A method for transmitting information for activity monitoring by an activity sensor device in an activity monitoring system comprising the activity sensor device worn by an individual, one or more occupancy sensor devices, and an activity monitoring server, the method comprising:
   detecting an individual's activity and classifying the detected signal;
   generating activity classification information by using the classified signal;
   establishing a connection to the one or more occupancy sensor devices; and
   transmitting the generated activity classification information and the individual's identification information to the connection-established occupancy sensor devices by using a first propagation with a short transmission range, so that the activity classification information and the individual's identification information can be transmitted along with occupancy information to the activity monitoring server,
   wherein the activity sensor device transmits the generated activity classification information and the individual's identification information to the one or more occupancy sensor devices or the activity monitoring server, and
   wherein the activity sensor device transmits the generated activity classification information and the individual's identification information to the one or more occupancy sensor devices having a first power,
   wherein the activity sensor device transmits the generated activity classification information and the individual's identification information to the activity monitoring server having a second power, and
   wherein the first power is less than the second power.

16. The method of claim 15, further comprising:
   storing the activity classification information in a database unless the activity sensor device is connected to the one or more occupancy sensor devices.

17. The method of claim 16, wherein unless the activity sensor device is connected to the one or more occupancy sensor devices, the activity classification information and the individual's identification information are directly transmitted to the activity monitoring server by using a third propagation with a broad transmission range.

18. The method of claim 15, wherein the occupancy information is periodically transmitted by the occupancy sensor device to the activity monitoring server.

19. The method of claim 15, wherein the occupancy information is transmitted by the occupancy sensor device to the activity monitoring server, only when a signal is received from the activity sensor device.

20. The method of claim 15, wherein the activity classification information and the individual's identification information are transmitted along with the occupancy information to the activity monitoring server, only when a connection to the one or more occupancy sensor devices is established.

21. An activity monitoring system comprising:
   an activity sensor device configured to detect an individual's physical activity, classify the detected physical activity, and transmit activity classification information as a result along with the individual's identification information;
   one or more occupancy sensor devices configured to receive the activity classification information and the individual's identification information from the activity sensor device, and transmit the received information along with occupancy information; and
   an activity monitoring server configured to manage the activity classification information, the occupancy information, and the individual's identification information received from the occupancy sensor devices,
   wherein the activity sensor device transmits the activity classification information and the individual's identification information at a first power and a second power, and
   where the activity sensor only transmits the activity classification information and the individual's identification information at the first power after a connection is established between the activity sensor device and the one or more occupancy sensor devices.

* * * * *